(12) United States Patent
Mabille et al.

(10) Patent No.: US 8,785,622 B2
(45) Date of Patent: Jul. 22, 2014

(54) CROSSLINKED POLYSACCHARIDES AND METHODS OF PRODUCTION THEREOF

(75) Inventors: Caroline Mabille, Paris (FR); Kraig Luczak, Cranbury, NJ (US)

(73) Assignee: Rhodia Operations, Aubervilliers (FR)

( * ) Notice: Subject to any disclaimer, the term of this patent is extended or adjusted under 35 U.S.C. 154(b) by 585 days.

(21) Appl. No.: 12/322,288

(22) Filed: Jan. 30, 2009

(65) Prior Publication Data

US 2009/0197829 A1    Aug. 6, 2009

Related U.S. Application Data

(60) Provisional application No. 61/024,965, filed on Jan. 31, 2008, provisional application No. 61/135,481, filed on Jul. 21, 2008.

(51) Int. Cl.
*A61K 31/715* (2006.01)
*A61K 31/717* (2006.01)
*A61K 31/718* (2006.01)

(52) U.S. Cl.
USPC .......... 536/56; 536/106; 536/114; 536/123.1; 536/124

(58) Field of Classification Search
CPC ............ C08B 37/0096; C08B 37/0093; C08B 37/0087; C08B 37/0051; C08B 37/0033; C08B 31/006
USPC ............ 536/56, 106, 114, 123.1, 124; 514/54
See application file for complete search history.

(56) References Cited

U.S. PATENT DOCUMENTS

| | | | |
|---|---|---|---|
| 3,301,723 A | 1/1967 | Chrisp et al. | 149/20 |
| 3,350,386 A * | 10/1967 | Engelskirchen et al. | 536/114 |
| 4,363,669 A | 12/1982 | Cottrell et al. | 106/205 |
| 4,677,201 A | 6/1987 | Morgan | 536/114 |
| 5,104,436 A | 4/1992 | Lauderdale et al. | 71/27 |
| 6,320,043 B1 | 11/2001 | Weber et al. | 536/84 |
| 2004/0208709 A1 | 10/2004 | Marsden | 405/264 |
| 2005/0112077 A1 | 5/2005 | Norman et al. | 424/70.13 |
| 2005/0227902 A1 | 10/2005 | Erazo-Majewicz et al. | 510/470 |
| 2006/0045861 A1 | 3/2006 | Bejger et al. | 424/70.13 |
| 2008/0112906 A1 | 5/2008 | Erazo-Majewicz et al. | 424/59 |
| 2008/0112907 A1 | 5/2008 | Chan et al. | 424/59 |

FOREIGN PATENT DOCUMENTS

| | | | | |
|---|---|---|---|---|
| CA | 2063365 | 10/1991 | | C08B 37/00 |
| EP | WO 03/078474 A1 | 9/2003 | | C08B 37/00 |
| EP | WO 2004/065433 A1 | 8/2004 | | C08F 18/08 |
| EP | WO 2008/058768 A1 | 5/2008 | | C08B 37/14 |
| JP | 2001-508116 | 6/2001 | | C08B 11/193 |
| JP | 2004/217590 | 8/2004 | | A61K 8/00 |
| WO | WO 2008/057425 A1 | 5/2008 | | A61K 8/73 |
| WO | WO 2008/076178 A1 | 6/2008 | | A61K 8/19 |

* cited by examiner

*Primary Examiner* — Shaojia Anna Jiang
*Assistant Examiner* — Bahar Craigo

(57) ABSTRACT

A substantially boron-free method for making a cationic guar comprises reacting particles of polysaccharide with a derivatizing agent to produce derivatized polysaccharide particles, washing the derivatized polysaccharide particles, and contacting, prior to or after the washing step, the particles with a glyoxal compound in order to crosslink the derivatized polysaccharide particles. Also disclosed are methods for making crosslinked derivatized polysaccharides, comprising (a) contacting particles of a polysaccharide with a titanium compound in an aqueous medium having an alkaline pH under conditions appropriate to intra-particulately crosslink the particles; (b) reacting, prior to or after the step of contacting the particles of polysaccharide with the titanium compound, the particles of polysaccharide with a derivatizing agent under conditions appropriate to produce derivatized polysaccharide particles; (c) washing the titanium crosslinked and derivatized particles; (d) contacting, concurrently with or after the step of washing the titanium crosslinked and derivatized particles, such particles with an aqueous medium having an acidic pH under conditions appropriate to substantially de-crosslink the particles; and (e) contacting, concurrently with or after step (d), the de-crosslinked particles with a glyoxal compound under conditions appropriate to intra-particulately crosslink the particles. The crosslinked cationic guar of the present invention is especially useful in home and personal care formulations, especially formulations comprising silicone since it improves silicone deposition.

15 Claims, No Drawings

CROSSLINKED POLYSACCHARIDES AND METHODS OF PRODUCTION THEREOF

CROSS REFERENCE TO RELATED APPLICATIONS

This application claims the benefit of U.S. Provisional Application Ser. No. 61/024,965, filed Jan. 31, 2008 and U.S. Provisional Application Ser. No. 61/135,481, filed Jul. 21, 2008, all herein incorporated by reference.

BACKGROUND OF THE INVENTION

The present invention relates to crosslinked polysaccharides and methods of preparation thereof and, in particular, glyoxal and glyoxal/titanium crosslinked guar and methods of preparation thereof.

Guars are commercially available in several forms, including derivatized and underivatized. Among the derivatized forms are cationic, non-ionic, and anionic, and combinations of cationic, non-ionic, and anionic. Among the derivatized guar splits and gums are carboxyl methyl guar gums, hydroxypropyl guar gums, and hydroxypropyl trimethylammonium guar gums, which are commercially available materials used in a variety of applications and are typically made by a "water-splits" process, wherein material, known as guar "splits", derived from guar seeds undergoes reaction with a derivatizing agent in an aqueous medium.

These various types of guars have been used extensively in many fields. Among the fields of use where properties of guars are useful are personal care, household care, and pet care formulations, including but not limited to: shampoos, body washes, hand soaps, lotions, creams, conditioners, shaving products, facial washes, neutralizing shampoos, personal wipes, other hair care products and skin treatments.

Guars are conventionally produced by milling at an alkaline pH and then crosslinked with Borax (sodium tetra borate). Borax is commonly used as a processing aid in the reaction step of the water-splits process to partially crosslink the surface of the guar splits and thereby reduces the amount of water absorbed by the guar splits during washing. The borate crosslinking takes place under alkaline conditions and is reversible, allowing the product to hydrate under acidic conditions.

However, due to regulatory concerns regarding the boron content of materials used in personal care applications, it has now become desirable to make derivatized guar without using any boron-containing crosslinker.

Another problem with conventional cationic guars is the production of trimethylamine ("TMA") impurity when milling at high temperatures. Trimethylamine is an undesirable impurity in personal care formulations due to its fishy smell.

A still further problem with conventional guars is undesirable yellowing whereas certain end use formulations require white guar.

What is needed is an alternative to boron crosslinking as a process aid to simplify the manufacture and handling of polysaccharide thickeners, including derivatized polysaccharide thickeners, such as derivatized guars.

It is also desirable to produce improved guars which are crosslinked, boron-free, and comprise substantially no trimethylamine or no trimethylamine at all.

It is further desired to provide cationic guars which improve silicone deposition in personal care formulations.

SUMMARY OF THE INVENTION

In one aspect, the present invention is directed to a method for making crosslinked derivatized polysaccharides, comprising the steps of: (a) contacting particles of a polysaccharide with a titanium compound in an aqueous medium having an alkaline pH under conditions appropriate to intra-particulately crosslink the particles; (b) reacting, prior to or after the step of contacting the particles of polysaccharide with the titanium compound, the particles of polysaccharide with a derivatizing agent under conditions appropriate to produce derivatized polysaccharide particles; (c) washing the titanium crosslinked and derivatized particles; (d) contacting, concurrently with or after the step of washing the titanium crosslinked and derivatized particles, such particles with an aqueous medium having an acidic pH under conditions appropriate to substantially de-crosslink the particles; and (e) contacting, concurrently with or after step (d), the de-crosslinked particles with a glyoxal compound under conditions appropriate to intra-particulately crosslink the particles.

In another aspect, present invention is directed to a method for making crosslinked derivatized polysaccharides, comprising the steps of: (a) contacting particles of a polysaccharide with a titanium compound in an aqueous medium having a pH greater than about 10 under conditions appropriate to intra-particulately crosslink the particles; (b) reacting, prior to or after the step of contacting the particles of polysaccharide with the titanium compound, the particles of polysaccharide with a derivatizing agent under conditions appropriate to produce derivatized polysaccharide particles; (c) washing the titanium crosslinked and derivatized particles; (d) contacting such particles with an aqueous medium having an acidic pH under conditions appropriate to substantially de-crosslink the particles; and (e) contacting, concurrently with or after step (d), the de-crosslinked particles with a glyoxal compound under conditions appropriate to intra-particulately crosslink the particles.

In a further aspect, the present invention is directed to a method for making crosslinked derivatized polysaccharides, comprising the steps of: (a) contacting particles of a polysaccharide with a titanium compound in an aqueous medium having pH greater than about 10 under conditions appropriate to intra-particulately crosslink the particles; (b) reacting, prior to or after the step of contacting the particles of polysaccharide with the titanium compound, the particles of polysaccharide with a derivatizing agent under conditions appropriate to produce derivatized polysaccharide particles; (c) washing the titanium crosslinked and derivatized particles; (d) contacting the titanium crosslinked and derivatized particles with an aqueous medium having a pH less than about 10 under conditions appropriate to substantially de-crosslink the particles; and (e) contacting the de-crosslinked particles with a glyoxal compound in an aqueous medium having a pH less than about 7 under conditions appropriate to intra-particulately crosslink the particles. In one embodiment, the aforementioned steps of contacting the titanium crosslinked and derivatized particles with an aqueous medium in step (d), contacting the de-crosslinked particles with a glyoxal compound in step (e) or both is performed through spraying.

In yet a further aspect, the present invention is directed to a method for producing a crosslinked polysaccharide comprising: (a) reacting particles of polysaccharide with a derivatizing agent under conditions appropriate to produce derivatized polysaccharide particles; (b) washing the derivatized polysaccharide particles; and (c) contacting, prior to or after the step of washing the derivatized polysaccharide particles, the particles with a glyoxal compound in an aqueous medium under condition appropriate to crosslink the derivatized polysaccharide particles.

In another aspect, the present invention is a personal care product comprising the polysaccharides made by any of the methods described above.

DETAILED DESCRIPTION

The guar made according to the method of the present invention has no intentionally added boron, but may comprise small amounts of boron impurities, for example, as a naturally occurring component of guar splits or process fluids used in the method.

The boron content of the material, as determined by mass spectroscopy, is less than about 50 parts per million (ppm") boron, that is, less than about 50 parts by weight boron per one million parts by weight of the material, more typically less than about 20 ppm, and even more typically less than 5 ppm.

As used herein, the terminology "aqueous medium" generally means a liquid medium that contains water, typically greater than or equal to 10 wt % water, more typically greater than or equal to 25 wt % water, even more typically greater than or equal to 50 wt % water and less than 90 wt %, more typically less than 75 wt %, and even more typically less than 50 wt % of one or more water miscible organic liquids, such as for example, an alcohol, such as ethanol or iso-propanol, and may, optionally contain one or more solutes dissolved in the aqueous medium. In one embodiment, the liquid portion of an aqueous medium consists essentially of water. As used herein the terminology "aqueous solution" refers more specifically to an aqueous medium that further comprises one or more solutes dissolved in the aqueous medium.

As used herein, the term "intra-particulately" means within each discrete particle of the polysaccharide and intra-particulate crosslinking thus refers to crosslinking between polysaccharide molecules of a discrete polysaccharide particle, typically between hydroxyl groups of such polysaccharide molecules, with no significant crosslinking between particles.

Suitable polysaccharides contain polymeric chains of saccharide constitutive units, and include, for example, starches, celluloses, xanthans, such as xanthan gum, polyfructoses such as levan, and galactomannans such as guar gum, locust bean gum, and tara gum. The polysaccharides are not completely soluble in the aqueous medium and thus typically remain as a discrete solid phase dispersed in the aqueous medium.

In one embodiment, the polysaccharide is a locust bean gum. Locust bean gum or carob bean gum is the refined endosperm of the seed of the carob tree, *Ceratonia siliqua*. The ratio of galactose to mannose for this type of gum is about 1:4. In one embodiment, the polysaccharide is a tara gum. Tara gum is derived from the refined seed gum of the tara tree. The ratio of galactose to mannose is about 1:3.

In one embodiment, the polysaccharide is a polyfructose. Levan is a polyfructose comprising 5-membered rings linked through β-2,6 bonds, with branching through β-2,1 bonds. Levan exhibits a glass transition temperature of 138° C. and is available in particulate form. At a molecular weight of 1-2 million, the diameter of the densely-packed spherulitic particles is about 85 nm.

In one embodiment, the polysaccharide is a xanthan. Xanthans of interest are xanthan gum and xanthan gel. Xanthan gum is a polysaccharide gum produced by *Xathomonas campestris* and contains D-glucose, D-mannose, D-glucuronic acid as the main hexose units, also contains pyruvate acid, and is partially acetylated.

In one embodiment, the polysaccharide of the present invention is derivatized or non-derivatized guar. Guar comes from guar gum, the mucilage found in the seed of the leguminous plant *Cyamopsis tetragonolobus*. The water soluble fraction (85%) is called "guaran," which consists of linear chains of (1,4)-β-D mannopyranosyl units-with α-D-galactopyranosyl units attached by (1,6) linkages. The ratio of D-galactose to D-mannose in guaran is about 1:2. Guar gum typically has a weight average molecular weight of between 2,000,000 and 5,000,000 Daltons.

The guar seeds used to make guar gum are composed of a pair of tough, non-brittle endosperm sections, hereafter referred to as "guar splits," between which is sandwiched the brittle embryo (germ). After dehulling, the seeds are split, the germ (43-47% of the seed) is removed by screening. The splits typically contain about 78-82% galactomannan polysaccharide and minor amounts of some proteinaceous material, inorganic salts, water-insoluble gum, and cell membranes, as well as some residual seedcoat and seed embryo.

Processes for making derivatives of polysaccharides are generally known. Typically, the polysaccharide is reacted with one or more derivatizing agents under appropriate reaction conditions to produce a guar polysaccharide having the desired substituent groups. Suitable derivatizing reagents are commercially available and typically contain a reactive functional group, such as an epoxy group, a chlorohydrin group, or an ethylenically unsaturated group, and at least one other substituent group, such as a cationic, nonionic or anionic substituent group, or a precursor of such a substituent group per molecule, wherein substituent group may be linked to the reactive functional group of the derivatizing agent by bivalent linking group, such as an alkylene or oxyalkylene group. Suitable cationic substituent groups include primary, secondary, or tertiary amino groups or quaternary ammonium, sulfonium, or phosphinium groups. Suitable nonionic substituent groups include hydroxyalkyl groups, such as hydroxypropyl groups. Suitable anionic groups include carboxyalkyl groups, such as carboxymethyl groups. The cationic, nonionic and/or anionic substituent groups may be introduced to the guar polysaccharide chains via a series of reactions or by simultaneous reactions with the respective appropriate derivatizing agents.

In one embodiment, the derivatized guar of the present invention includes but is not limited to hydroxypropylguar (HPG), carboxymethylguar (CMG), hydroxyethyl guar (HEG), carboxymethylhydroxypropyl guar (CMHPG), hydroxybutyl guar (HBG), cationic guar, hydrophobically modified guar (HMG), hydrophobically modified carboxymethylguar (HMCMG), hydrophobically modified hydroxyethylguar (HMHEG), hydrophobically modified hydroxypropylguar (HMHPG), hydrophobically modified carboxymethylhydroxypropylguar (HMCMHPG), hydrophobically modified hydroxybutyl guar (HMHBG), and hydrophobically modified cationic guar (HMCG).

In one embodiment, the polysaccharide is reacted with an alkylene oxide derivatizing agent, such as ethylene oxide, propylene oxide, or butylene oxide, under known alkoxylation conditions to add hydroxyalkyl and/or poly(alkyleneoxy) substituent groups to the guar polysaccharide chains.

In one embodiment, the polysaccharide is reacted with a carboxylic acid derivatizing agent, such as sodium monochloroacetate, under known esterification conditions to add carboxyalkyl groups to the guar polysaccharide chains.

The derivatizing agent can comprise a cationic substituent group that comprises a cationic nitrogen radical, more typically, a quaternary ammonium radical, for example. Typical quaternary ammonium radicals are trialkylammonium radicals, such as trimethylammonium radicals, triethylammonium radicals, tributylammonium radicals, aryldialkylammonium radicals, such as benzyldimethylammonium radicals, radicals, and ammonium radicals in which the nitrogen atom is a member of a ring structure, such as pyridinium radicals and imidazoline radicals, each in combination with a counterion, typically a chloride, bromide, or iodide counterion. In some embodiments, the cationic substituent group is linked to the reactive functional group of the cationizing agent, for example, by an alkylene or oxyalkylene linking group.

Suitable cationizing reagents include, for example, epoxy-functional cationic nitrogen compounds, such as, for example, 2,3-epoxypropyltrimethylammonium chloride; chlorohydrin-functional cationic nitrogen compounds, such as, for example, 3-chloro-2-hydroxypropyl trimethylammonium chloride, 3-chloro-2-hydroxypropyl-lauryldimethylammonium chloride, 3-chloro-2-hydroxypropyl-stearyldimethylammonium chloride; and vinyl-, or (meth) acrylamide-functional nitrogen compounds, such as methacrylamidopropyl trimethylammonium chloride.

While the embodiments detailed below discuss the use of derivatized guar, it is understood that any polysaccharide detailed above may be used.

In some embodiments the guar splits are reacted with a chlorohydrin-functional quaternary ammonium compound in the presence of base, in an aqueous medium under relatively mild conditions, such as heating to a temperature of about 20° C. to about 85° C., typically about 40° C. to about 70° C., to produce cationic guar splits, that is, derivatized guar splits having cationic functional groups.

The derivatized guar splits can comprise molecules of guar having one or more substituent groups per molecule of guar, wherein a first portion of the substituent groups is added by reaction of guar splits with one or more first derivatizing agents under appropriate reaction conditions in a first liquid medium, and a second portion of the substituent groups have been added by reaction of the guar splits with one or more second derivatizing agents in a second liquid medium under appropriate reaction conditions, wherein at least one of the first liquid medium and the second liquid medium is an aqueous medium.

The derivatized guar splits produced by reaction of guar splits with a derivatizing agent in an aqueous medium can be in the form of water-swollen gum comprising (i) from about 30 to 60 parts by weight ("pbw"), more typically from 30 to 50 pbw of cationic guar splits per 100 pbw of water-swollen gum and (ii) from about 40 to 70 pbw, more typically 50 to 70 pbw of water per 100 pbw of water-swollen gum.

The step of contacting the derivatized guar splits with an aqueous wash medium can be conducted prior to, concurrent with or after the step of the reaction of guar splits with a derivatizing agent in an aqueous reaction medium under appropriate reaction conditions. In one embodiment, the water-swollen gum produced by reaction of guar splits with a derivatizing agent in an aqueous reaction medium is contacted with the aqueous wash medium.

The derivatized guar splits can then be allowed to cool, typically to a temperature of less than or equal to about 50° C. prior to washing the derivatized guar splits.

The derivatized guar splits can then be washed with the aqueous medium by contacting the derivatized guar splits with the aqueous medium and then physically separating the aqueous wash medium, in the form of an aqueous rinse solution, from the derivatized guar splits, wherein the contacting and separating steps taken together constitute one "wash step" or "washing" step. In one embodiment, an aqueous wash medium comprising from about 0.1 to about 30 pbw of a glyoxal can be used.

One or more wash steps are conducted in any suitable process vessel. Each wash step may be conducted as a batch process, such as for example, in a stirred mixing vessel, or as a continuous process, such as for example, in a column wherein a stream of the derivatized guar splits is contacted with a co-current or counter-current stream of aqueous wash medium.

The aqueous wash medium can comprise water and, optionally, up to 25 pbw water miscible organic liquid per 100 pbw of aqueous medium. Suitable water miscible organic liquids include, for example, alcohols such as methanol or ethanol. More typically, the aqueous wash medium consists essentially of water, even more typically, of deionized water.

The derivatized guar splits can be contacted with, for example, from about 2 to about 30 kilograms ("kg"), more typically from about 5 to about 20 kg, even more typically from about 5 to about 15 kg, of aqueous wash medium per kg of derivatized guar splits solids per wash step.

The process of derivatizing guar particles or "splits" and one or more wash steps are discussed above; one or more methods of crosslinking the derivatized guar particles will now be discussed. In one embodiment, a method for producing crosslinked guar particles comprises (a) reacting guar particles with a derivatizing agent, as discussed above; (b) washing the derivatized guar particles, as discussed above; and (c) contacting (prior to, concurrently with or after the step of washing the derivatized polysaccharide particles) the guar particles with a glyoxal compound in an aqueous medium under condition appropriate to crosslink the derivatized polysaccharide particles.

In one embodiment, the crosslinking step can be conducted by contacting the derivatized guar splits with glyoxal-containing aqueous wash medium, to at least partially crosslink the hydroxyl groups of the respective guar particles, for a contact time of up to about 30 minutes, more typically from about 30 seconds to about 15 minutes, even more typically from about 1 minute to about 8 minutes, per high salt wash step.

In another embodiment, the crosslinking step involves contacting the derivatized guar splits with a glyoxal compound after an aqueous wash step. The glyoxal compound is typically in an aqueous solution comprising from about 0.1 to about 30 pbw of glyoxal per 100 pbw of the total mixture. The mixture may also contain an effective amount of an acid to lower the pH below 7. Contacting the derivatized guar splits with a glyoxal compound at least partially crosslinks the hydroxyl groups of the respective guar particles. Crosslinking typically takes place intra-particulately, that is, within each discrete particle of guar splits, between the hydroxyl groups of the particle, without any significant crosslinking between guar splits particles. Contacting the derivatized guar splits with glyoxal compound may comprise various methods including but not limited to a spraying process.

In another embodiment, titanium compounds are contacted with the derivatized or underivatized guar particles prior to or concurrently with the first wash step. Contacting the guar particles with titanium compounds in such a manner at least partially crosslinks the hydroxyl groups of the respective guar particles, thus making the guar particles less susceptible to loss during the wash step, i.e, when physically separating the aqueous wash medium, in the form of an aqueous rinse solution, from the derivatized guar splits. This, in turn, likely increases total derivatized guar yield.

Typically, an aqueous dispersion of the titanium crosslinked guar is maintained at a pH of greater than or equal to about 8, more typically greater than or equal to about 10, more typically greater than or equal to about 12, to maintain the guar in the form of substantially water insoluble crosslinked particles to maintain the fluidity of the aqueous dispersion. Crosslinking of the titanium crosslinked guar, however, is reversible and the kinetics of de-crosslinking are pH sensitive. Generally, the titanium crosslinked guar particles are de-crosslinked in a solution having a pH of less than about 8. The rate at which de-crosslinking of the guar particles occurs typically increases with decreasing pH. The de-crosslinking rate can be increased by adjusting the pH of the aqueous medium to a value of less than or equal to about 8, more typically less than or equal to about 7 and allows dissolution of the de-crosslinked guar in the aqueous medium, typically to form a viscous aqueous solution of the guar in the aqueous medium. The de-crosslinked guar can then be again crosslinked with a glyoxal compound to maintain the guar particles in the form of an acid dispersion of substantially water insoluble crosslinked particles (thus maintaining the fluidity of the aqueous dispersion). It is desirable in certain formulations to utilize crosslinked guar particles in an acid dispersion.

In the above-mentioned embodiment, a method for producing crosslinked guar particles comprises: (a) contacting guar particles with a titanium compound in an aqueous medium having an alkaline pH under conditions appropriate to intra-particulately crosslink the particles; (b) reacting, prior to or after the step of contacting the guar particles with the titanium compound, the guar particles with a derivatizing agent under conditions appropriate to produce derivatized guar particles; (c) washing the titanium crosslinked and derivatized particles; (d) contacting, concurrently with or after the step of washing the titanium crosslinked and derivatized particles, such particles with an aqueous medium having an acidic pH under conditions appropriate to substantially de-crosslink the particles; and (e) contacting, concurrently with or after step (d), the de-crosslinked particles with a glyoxal compound under conditions appropriate to intra-particulately crosslink the particles.

Suitable titanium compounds are those titanium (II), Titanium (III), titanium (IV), and titanium (VI) compounds that are soluble in the aqueous medium. In one embodiment, the titanium compound is a titanium (IV) compound, that is, a titanium compound in which the titanium atoms of the compound are in the +4 oxidation state.

In one embodiment, the titanium compound is a titanium salt, more typically a water soluble titanium salt, such as titanium tetrachloride, titanium tetrabromide, or tetra amino titanate.

In one embodiment, the titanium compound comprises one or more titanium chelates. Suitable titanium chelates are commercially available and include but are not limited to titanium acetylacetonates, triethanolamine titanates, and titanium lactates In one embodiment, the titanium compound comprises one or more titanium esters. Suitable titanium esters are commercially available and include but are not limited to n-butyl polytitanates, titanium tetrapropanolate, octyleneglycol titanates, tetra-n-butyl titanates, tetra-n-buytl titanates, tetra-2-ethylhexyl titanates, tetra-isopropyl titanate, and tetra-isopropyl titanate.

In one embodiment, the titanium compound is selected from diisopropyl di-triethanolamino titanate, titanate (2-), dihydroxy bis [2-hydroypropanato (2-)-O1, O2], ammonium salt, titanium acetylacetonate, titanium ortho ester, titanium (IV) chloride, and mixtures thereof.

In one embodiment, the guar particles are contacted with the titanium compound in the aqueous medium under conditions appropriate to at least partially intra-particulately crosslink the hydroxyl groups of the respective guar particles.

In one embodiment, aqueous medium comprises, based on 100 pbw of the medium, from about 0.1 to about 15 pbw, more typically from about 0.5 to about 10 pbw, and even more typically from about 1 to about 5 pbw, of the titanium compound.

In one embodiment, guar particles are contacted with titanium compound in the aqueous medium at a temperature of from about 10 to about 90° C., more typically from about 15 to about 35° C., and even more typically, from about 20 to about 30° C.

In one embodiment, the guar particles are contacted with titanium compound in the aqueous medium for a time period of from about 1 minute to about 2 hours, more typically from about 5 minutes to about 60 minutes, and even more typically from about 15 to about 35 minutes.

It is also understood that the guar particles can be first contacted with a glyoxal compound, then washed, then de-crosslinked under alkaline conditions, then crosslinked with a titanium compound, to form crosslinked guar particles utilized in an alkaline dispersion. In one embodiment, a method for producing crosslinked guar particles comprises: (a) contacting guar particles with a glyoxal compound in an aqueous medium under conditions appropriate to intra-particulately crosslink the particles; (b) reacting, prior to or after the step of contacting the guar particles with the glyoxal compound, the guar particles with a derivatizing agent under conditions appropriate to produce derivatized guar particles; (c) washing the glyoxal crosslinked and derivatized particles; (d) contacting, concurrently with or after the step of washing the glyoxal crosslinked and derivatized particles, such particles with an aqueous medium having an pH appropriate to substantially de-crosslink the particles; and (e) contacting, concurrently with or after step (d), the de-crosslinked particles with a titanium compound under conditions appropriate to intra-particulately crosslink the particles.

The washed derivatized splits can be separated from the aqueous wash medium by any suitable dewatering means such as for example, filtration and/or centrifugation. In one embodiment, the washed derivatized splits are separated from the wash liquid by centrifugation.

The dewatered derivatized splits can have a water content of less than or equal to about 90 wt.%, more typically less than or equal to about 85 wt. % and even more typically less than or equal to about 80 wt. %.

The dewatered guar splits are dried and ground to produce derivatized guar particles.

The guar can be dried by any suitable drying means, such as, for example, air drying, fluid bed drying, flash grinding, freeze drying, to a moisture content of less than or equal to about 20 wt %, more typically less than or equal to about 15 wt %.

The dried guar splits can be ground by any suitable particle size reduction means, such as, for example, a grinding mill. In one embodiment the guar splits are simultaneously dried and ground in a "flash milling" procedure, wherein a stream of guar splits and a stream of heated air are simultaneously introduced into a grinding mill.

The guar according to the present invention is especially useful in personal, household, and pet care applications, such as, for example, shampoos, body washes, hand soaps, lotions, creams, conditioners, shaving products, facial washes, neutralizing shampoos, personal wipes, and skin treatments.

The personal care compositions comprise cationic guar of the invention and one or more "benefit agents" that is, materials known in the art that provide a personal care benefit, such as moisturizing or conditioning, to the user of the personal care composition, such as, for example, cleansing agents such as anionic surfactants, cationic surfactants, amphoteric surfactants, zwitterionic surfactants and non-ionic surfactants, as well as emollients, moisturizers, conditioners, polymers, vitamins, abrasives, UV absorbers, antimicrobial agents, anti-dandruff agents, fragrances, depigmentation agents, reflectants, thickening agents, detangling/wet combing agents, film forming polymers, humectants, amino acid agents, antimicrobial agents, allergy inhibitors, anti-acne agents, anti-aging agents, anti-wrinkling agents, antiseptics, analgesics, antitussives, antipruritics, local anesthetics, anti-hair loss agents, hair growth promoting agents, hair growth inhibitor agents, antihistamines, antiinfectives, inflammation inhibitors, anti-emetics, anticholinergics, vasoconstrictors, vasodilators, wound healing promoters, peptides, polypeptides and proteins, deodorants and anti-perspirants, medicament agents, hair softeners, tanning agents, skin lightening agents, depilating agents, shaving preparations, external analgesics, counterirritants, hemorrhoidals, insecticides, poison ivy products, poison oak products, burn products, anti-diaper rash agents, prickly heat agents, make-up preparations, amino acids and their derivatives, herbal extracts, retinoids, flavoids, sensates, anti-oxidants, hair lighteners, cell turnover enhancers, coloring agents, and mixtures thereof.

The cationic guars of the invention aid in the delivery of the benefit agent onto and/or into the skin, hair, and/or nails.

The personal care composition according to the present invention can be an aqueous composition that comprises, based on 100 pbw of the composition:

(a) greater than about 0.001 pbw, more typically from about 0.01 to about 0.8 pbw, and even more typically from about 0.1 to about 0.4 pbw, of a derivatized guar according to the present invention, and (b) greater than about 1 pbw, typically from about 5 to about 20 pbw, and even more typically from about 10 to about 15 pbw, of a surfactant selected from cationic surfactants, anionic surfactants, amphoteric surfactants, zwitterionic surfactants, nonionic surfactants, and mixtures thereof.

The surfactant component (b) the personal care composition according to the present invention can comprise a zwitterionic surfactant, more typically a zwitterionic surfactant selected from alkyl betaines and amidoalkylbetaines.

The surfactant component (b) the personal care composition according to the present invention can comprise a mixture of a zwitterionic surfactant, more typically a zwitterionic surfactant selected from alkyl betaines and amidoalkylbetaines, and an anionic surfactant, more typically selected from salts of alkyl sulfates and alkyl ether sulfates.

Anionic surfactants suitable for use in the personal care compositions are well known in the art, and include, for example, ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, and mixtures thereof.

Amphoteric surfactants suitable for use in the compositions are well known in the art, and include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group such as carboxy, sulfonate, sulfate, phosphate, or phosphonate. In one embodiment, the amphoteric surfactant comprises at least one compound selected from cocoamphoacetate, cocoamphodiacetate, lauroamphoacetate, and lauroamphodiacetate.

Zwitterionic surfactants suitable for use in the personal care compositions are well known in the art, and include, for example, those surfactants broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. Specific examples of suitable Zwitterionic surfactants include alkyl betaines, such as cocodimethyl carboxymethyl betaine, lauryl dimethyl carboxymethyl betaine, lauryl dimethyl alpha-carboxy-ethyl betaine, cetyl dimethyl carboxymethyl betaine, lauryl bis-(2-hydroxy-ethyl)carboxy methyl betaine, stearyl bis-(2-hydroxy-propyl)carboxymethyl betaine, oleyl dimethyl gamma-carboxypropyl betaine, and lauryl bis-(2-hydroxypropyl)alpha-carboxyethyl betaine, amidopropyl betaines, and alkyl sultaines, such as cocodimethyl sulfopropyl betaine, stearyldimethyl sulfopropyl betaine, lauryl dimethyl sulfoethyl betaine, lauryl bis-(2-hydroxy-ethyl)sulfopropyl betaine, and alkylamidopropylhydroxy sultaines.

Nonionic surfactants suitable for use in the personal care compositions are well known in the art, and include, for example, long chain alkyl glucosides having alkyl groups containing about 8 carbon atoms to about 22 carbon atoms, coconut fatty acid monoethanolamides such as cocamide MEA, coconut fatty acid diethanolamides, and mixtures thereof.

The compositions can also comprise a conditioning agent. Organic conditioning oils for use in the personal care compositions may also comprise liquid polyolefins, more preferably liquid poly-.alpha.-olefins, more preferably hydrogenated liquid poly-.alpha.-olefins. Polyolefins for use herein are prepared by polymerization of $C_4$ to about $C_{14}$ olefenic monomers, preferably from about $C_6$ to about $C_{12}$. Conditioning agents suitable for use in the personal care composition are well known in the art, and include any material which is used to give a particular conditioning benefit to hair and/or skin. In hair treatment compositions, suitable conditioning agents are those which deliver one or more benefits relating to shine, softness, antistatic properties, wet-handling, damage, manageability, body, and greasiness. Conditioning agents useful in personal care compositions according to the present invention typically comprise a water insoluble, water dispersible, non-volatile, liquid that forms emulsified, liquid particles or are solubilized by the surfactant micelles, in an anionic surfactant component, as described above and include those conditioning agents characterized generally as silicones, such as silicone oils, cationic silicones, silicone gums, high refractive silicones, and silicone resins, and organic conditioning oils, such as hydrocarbon oils, polyolefins, and fatty esters.

In the case of personal care compositions comprising silicones, the cationic guar of the invention has been found to provide unexpectedly improved silicone deposition properties, which are very desirable in the art.

In certain embodiments, the derivatized guar gum of the invention aids in the delivery of the conditioning agent onto and/or into the skin, hair, and/or nails.

The personal care compositions according to the present invention may, optionally, further comprise other ingredients, in addition to benefit agents, such as, for example, preservatives such as benzyl alcohol, methyl paraben, propyl paraben, and imidazolidinyl urea, electrolytes, such as sodium chloride, sodium sulfate, and sodium citrate, thickeners, such as polyvinyl alcohol, pH adjusting agents such as citric acid and sodium hydroxide, pearlescent or opacifying agents, dyes, and sequestering agents, such as disodium ethylenediamine tetra-acetate.

In one embodiment, the boron-free guar of the invention is prepared by comprising reacting the guar with glyoxal at a pH of less than about 6, wherein no boron crosslinker is introduced. In certain embodiments about 0.01 to about 30 parts by weight glyoxal per 100 parts by weight guar is used. In certain embodiments Bronsted acid is reacted with alkaline guar to adjust pH to less than about 6 either prior to, simultaneously with, or after introducing the glyoxal to the guar.

A preferred Bronsted acid is citric acid, but acetic or other Bronsted acids can easily be used. The Bronsted acid is generally introduced at a concentration of about 1 to 100% is used to adjust the pH to less than about 6 and in some embodiments the pH is about 4.

The guar can be anionic, cationic, neutral, or derivatized with a combination of derivatizing agents. When the guar is cationic or derivatized with a combination of derivizing agents comprising a cationic agent, it is especially useful for personal care compositions which include an oil or particulate deliverable agent, in which case the absence of TMA odor is especially advantageous.

In the field of personal care compositions, one or more oily conditioning agents are usually included. Oily conditioning agents include materials which are used to give a particular conditioning benefit to hair and/or skin. In hair treatment compositions, suitable conditioning agents are those which deliver one or more benefits relating to shine, softness, combability, antistatic properties, wet-handling, damage, manageability, body, and greasiness. The oily conditioning agents useful in the personal care compositions typically comprise a water-insoluble, water-dispersible, non-volatile, liquid that forms emulsified, liquid particles. Suitable oily conditioning agents for use in the composition are those conditioning agents characterized generally as silicones (e.g., silicone oils, cationic silicones, silicone gums, high refractive silicones, and silicone resins), organic conditioning oils (e.g., hydrocarbon oils, polyolefins, and fatty esters) or combinations thereof, or those conditioning agents which otherwise form liquid, dispersed particles in the aqueous surfactant matrix herein. Other suitable organic conditioning oils for use as the conditioning agent in the personal care compositions include fatty esters having at least 10 carbon atoms. These fatty esters include esters with hydrocarbyl chains derived from fatty acids or alcohols. The hydrocarbyl radicals of the fatty esters hereof may include or have covalently bonded thereto other compatible functionalities, such as amides and alkoxy moieties (e.g., ethoxy or ether linkages, etc.).

Specific examples of preferred fatty esters include, but are not limited to, isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, and oleyl adipate.

Other fatty esters suitable for use in the personal care compositions are those known as polyhydric alcohol esters. Such polyhydric alcohol esters include alkylene glycol esters. Still other fatty esters suitable for use in the personal care compositions are glycerides, including, but not limited to, mono-, di-, and tri-glycerides, preferably di- and tri-glycerides, more preferably triglycerides. A variety of these types of materials can be obtained from vegetable and animal fats and oils, such as castor oil, safflower oil, cottonseed oil, corn oil, olive oil, cod liver oil, almond oil, avocado oil, palm oil, sesame oil, lanolin and soybean oil. Synthetic oils include, but are not limited to, triolein and tristearin glyceryl dilaurate.

Personal care formulations often comprise silicone. For example, in shampoo formulations, silicone is included for its hair conditioning property. Quality of shampoo formulations is often measured in terms of the amount of silicone which is deposited on hair in standardized tests.

The personal care compositions may also comprise an anti-dandruff active. Suitable non-limiting examples of anti-dandruff actives include pyridinethione salts, azoles, selenium sulfide, particulate sulfur, keratolytic agents, and mixtures thereof. Such anti-dandruff actives should be physically and chemically compatible with the essential components of the composition, and should not otherwise unduly impair product stability, aesthetics or performance.

Active ingredients can be any of the ones mentioned earlier, especially a silicone compound, an organic oil, an anti-dandruff active, a perfume, or combinations thereof.

One the several advantages of the invention is the dispersibility of the guar, and in some embodiments another advantage is the higher rate of deposition than that of the corresponding boron crosslinked guar.

Conditioners and shampoo compositions which include silicone oil and cationic guar made according to the above described method are very advantageous in that they have improved dispersion, deposition of silicone, are non-yellowing, and do not suffer from TMA odor.

The following examples in which all parts and percentages are by weight unless otherwise indicated are presented to illustrate a few embodiments of the invention.

EXAMPLES

1. Preparation of Glyoxal Cross-Linked Guars

Water, QUAT 188, sodium hydroxide, and guar splits are added to a ribbon blender and mixed. The mixture is then heated to 130 F and then held isothermal at 130 F for 1.5 hours. These splits are cooled, washed for 3 minutes at a ratio of 10:1 (water:splits), filtered and collected. To the wet splits, a 40% mixture of glyoxal in water is added to the splits and mixed for 10 minutes. Then, a 50% mixture of citric acid in water is added and mixed for 10 minutes. These splits are then milled using a flash grinder and collected as off-white powder. Below are the charges for examples CAT07038.2, CAT07038.3, CAT07038.4 which are JAGUAR C-14 types, and CAT07055.1 which is a JAGUAR C-17 type.

| CAT07038 | Grams |
|---|---|
| Splits | 5000 |
| Water | 2278 |
| NaOH (50%) | 472 |
| Quat 188 (65%) | 1710 |
| NaOH (50%) | 128 |
| Water | 1122 |
| Total | 10710 |

-continued

|  | CAT07038.2 | CAT07038.3 | CAT07038.4 |
|---|---|---|---|
| Splits (g/dry basis) | 1350 | 1350 | 1350 |
| Glyoxal (40%) | 28.4 | 14.4 | 7.4 |
| Citric Acid (50%) | 64.0 | 67.0 | 67.0 |
| Glyoxal (%) | 0.84% | 0.43% | 0.22% |

| CAT07055 | Grams |
|---|---|
| Splits | 5000 |
| Water | 2400 |
| NaOH (25%) | 1800 |
| Quat 188 (65%) | 2500 |
| Total | 11700 |

| | CAT07055.1 |
|---|---|
| Splits (g/dry basis) | 1300 |
| Glyoxal (40%) | 28.1 |
| Citric Acid (50%) | 100.0 |
| Glyoxal (%) | 0.87% |

H0708478C is a JAGUAR C-14 BFG that was produced with a similar process as the CAT07038.1, but at the plant scale. H0708476C is a JAGUAR C-17 BFG that was produced with a similar process as the CAT07055.1, but at the plant scale.

2. Preparation of Glyoxal Cross-Linked Guar Premix 90 parts by weight deionised water is charged in a mixing vessel. pH is adjusted to pH 4 using 20% citric acid solution. Then, 10 parts by weight cationic guar is added with continuous mixing. The guar premix is mixed for 15 min prior to be added in the main mixing vessel used for the shampoo preparation.

3. (Comparative) Preparation of Boron-Linked Guar Premix 90 parts by weight deionised water is charged in a mixing vessel. pH is adjusted to pH 12 using 50% NaOH solution. Then, 10 parts by weight boron cross-linked cationic guar is added with continuous mixing. The guar premix is mixed for 15 min prior to be added in the main mixing vessel used for the shampoo preparation.

4. Preparation of Surfactant Blend

The surfactants blend is prepared by charging the ingredients in a mixing vessel in the following sequence: 36.7 wt. % deionized water, 6.9 wt. % Mirataine BETC30 (30.74% active), 56.3 wt. % Empicol ESB-3M (26.5% active), 0.05 wt. % Kathon C G brand isothiazolone biocide. The blend is mixed until homogeneous.

5. Preparation of Shampoo

A shampoo is prepared by mixing the ingredients which are charged in the main mixing vessel in the following sequence: 93.9 parts by weight surfactants blend, 1.5 parts by weight dimethicone emulsion (65% active droplet size, approx 0.6 μm) Mirasil D M 500 000 emulsion, 3 parts by weight guar premix and 1.6 parts by weight NaCl. Between each addition, the shampoo is mixed until homogeneous. After salt addition, pH is checked and adjusted to pH 6.0-6.5 if needed using citric acid or NaOH solutions.

6. Measurement of Silicone Deposition

Deposition efficiency of shampoos is measured on Virgin Medium Brown Caucasian Hair (hair tress weight: 4.5 grams; length below epoxy blue clip: 20 cm) supplied by IHIP (International Hair Importers & Products Inc.). Two measurements are done per shampoo to derive the mean value and standard deviation.

The method contains 4 steps: A. the pre-treatment of the hair tresses with a 10% SLES (sodium lauryl ether sulfate) solution, B. the treatment of the hair tresses with the shampoo, C. the dimethicone extraction using THF (Tetrahydrofuran) and D. the dosage of the extracted dimethicone using GPC.

A. Hair pre-treatment: Hair tresses are pre-treated with a 10% SLES solution, then rinsed with water prior to be treated with the dimethicone-containing shampoo. The procedure is as follows: set the water flow rate to 150 ml/s and the water temperature to 38° C. Wet the hair tress under running water for 1 minute. Apply 3 ml of a 10% SLES solution along the hair tress. Rinse under running water for 1 minute.

B. Hair treatment: Weigh out precisely approx. 450 mg of shampoo. Roll the hair tress around the finger and withdraw the shampoo with it. Massage the product into the hair for 45 s. Make sure that the product is distributed evenly across the tress assembly. Rinse under running water for 30 s. Strip off excess water from the tress by pulling through middle finger and forefinger. Leave to dry and equilibrate overnight in a climatic room (21° C., 50% H.R.)

C. Silicone extraction: For each hair tress, tare a 250 ml polyethylene bottle. Introduce the hair tress in the bottle while maintaining the mounting tab outside the bottle. Cut the hair just below the mounting tab and record the amount of hair introduced in the bottle. Place the polyethylene bottle and introduce about 100 ml of THF in it. Cap the bottle. Place all the bottles on the agitation table and leave to mix for 24 hours at 200 rpm. Under the hood, transfer the THF extraction solution in a 150 ml evaporating dish. Leave to evaporate (maximum ventilation rate) for 24 hours under the hood.

D. Dosage of the extracted dimethicone: Tare the evaporating dish capped with a watch glass. Under the hood, introduce about 4 ml of THF in the evaporating dish. Using a spatula, re-dissolve the dimethicone deposited onto the walls of the evaporating dish. Once the silicone is re-solubilized, weigh the evaporating dish capped with the watch glass and record the amount of THF introduced. Using a syringe, transfer the dimethicone solution in a 2 ml vial and cap the vial. Dose the dimethicone concentration in the vial using GPC. The amount of dimethicone deposited on hair, Q, expressed in ppm (μg of dimethicone per g of hair) is calculated as follows:

$$Q(\mu g \text{ dimethicone per gram of hair}) = \frac{C_{dimethicone} \times m_{THF}}{m_{hair}}$$

where Cdimethicone is the dimethicone concentration in the GPC vial expressed in ppm (μg dimethicone per gram of THF), mTHF the amount of THF, expressed in grams, used to re-solubilize the dimethicone in the evaporating dish and mhair, the amount of hair expressed in grams introduced in the polyethylene bottle.

6. Silicone Deposition Measurement of Invention versus Prior Art

A first set of measurements resulted in the following:

| Crosslinker for Cationic Guar | Silicone Deposited | Standard Deviation |
|---|---|---|
| 1% glyoxal | 603 | 5 |
| 0.5% glyoxal | 588 | 23 |
| 0.25% glyoxal | 603 | 19 |
| Borax (comparative) | 512 | 6 |

A second set of measurements resulted in the following:

| Crosslinker for Cationic Guar | Silicone Deposited | Standard Deviation |
|---|---|---|
| 1% glyoxal | 604 | 17 |
| Borax (comparative) | 570 | 18 |

A third set of measurements resulted in the following:

| Crosslinker for Cationic Guar | Silicone Deposited | Standard Deviation |
|---|---|---|
| 1% glyoxal | 595 | 20 |
| 1% glyoxal | 590 | 18 |
| Borax | 461 | 25 |
| Borax | 536 | 22 |

The following method was used to measure color of guar powders.

For each product, 3 pellets having a diameter of 13 mm are prepared by pressing 710 mg of guar powder at 8 tons for 1 min using a 15-ton hydraulic press. On each pellet, 3 colour measurements are performed with a Konica Minolta Spectrophotometer CM-2600d/2500d in the L*a*b* system using the 10° observer and the illuminant D65 adjusted with UV. L*a*b* data recorded are the ones obtained in the specular-included geometry (SCI). b* coordinate reflects the yellowness degree. The higher the b* value, the higher the yellowness. From the 9 measurements done for each product, mean b* value and standard deviation are derived.

|  | Product | b* coordinate Blue (−)/Yellow (+) axis | Standard Deviation |
|---|---|---|---|
| C14-like | C14S batch 340D | 26.2 | 0.8 |
|  | CAT07038-2 | 10.6 | 0.1 |
|  | CAT07038-3 | 10.4 | 0.1 |
|  | CAT07038-4 | 10.3 | 0.1 |
|  | BFG-C14 batch H0708478C | 12.2 | 0.1 |
| C17-like | C17 batch 226D | 20.9 | 0.2 |
|  | CAT07055-1 | 11.7 | 0.1 |
|  | BFG-C17 batch H0708476C | 12.4 | 0.1 |

The present invention, therefore, is well adapted to carry out the objects and attain the ends and advantages mentioned, as well as others inherent therein. While the invention has been depicted and described and is defined by reference to particular preferred embodiments of the invention, such references do not imply a limitation on the invention, and no such limitation is to be inferred. The invention is capable of considerable modification, alteration and equivalents in form and function, as will occur to those ordinarily skilled in the pertinent arts. The depicted and described preferred embodiments of the invention are exemplary only and are not exhaustive of the scope of the invention. Consequently, the invention is intended to be limited only by the spirit and scope of the appended claims, giving full cognizance to equivalents in all respects.

What is claimed is:

1. A method for producing crosslinked derivatized polysaccharides, comprising:
    (a) contacting particles of a polysaccharide with a titanium compound in an aqueous medium having an alkaline pH under conditions appropriate to intra-particulately crosslink the particles;
    (b) reacting, prior to or after the step of contacting the particles of polysaccharide with the titanium compound, the particles of polysaccharide with a derivatizing agent under conditions appropriate to produce derivatized polysaccharide particles;
    (c) washing the titanium crosslinked and derivatized particles;
    (d) contacting, concurrently with or after the step of washing the titanium crosslinked and derivatized particles, such particles with an aqueous medium having an acidic pH under conditions appropriate to substantially de-crosslink the particles; and
    (e) contacting, concurrently with or after step (d), the de-crosslinked particles with a glyoxal compound under conditions appropriate to intra-particulately crosslink the particles.

2. The method of claim 1 wherein the titanium compound is selected from the group consisting of titanium salts, titanium chelates and titanium esters.

3. The method of 1 wherein the titanium compound is selected from the group consisting of titanium tetrachloride, titanium tetrabromide, tetra amino titanate, titanium acetylacetonate, triethanolamine titanate, titanium lactate, n-butyl polytitanate, titanium tetrapropanolate, octyleneglycol titanate, tetra-n-butyl titanate, tetra-2-ethylhexyl titillate, tetra-isopropyl titanate, diisopropyl di-triethanolamino titanate, titanium ortho ester, titanium (IV) chloride and mixtures thereof.

4. The method of claim 1 wherein contacting the titanium crosslinked and derivatized particles with an aqueous medium in step (d), contacting the de-crosslinked particles with a glyoxal compound in step (e) or both is performed through a spraying process.

5. The method of claim 1 wherein about 0.01 to about 30 parts by weight of the glyoxal compound per 100 parts by weight of the derivatized polysaccharide particles is utilized to intra-particulately crosslink the particles.

6. The method of claim 5 wherein about 0.1 to about 30 parts by weight of the glyoxal compound per 100 parts by weight of the derivatized polysaccharide particles is utilized to intra-particulately crosslink the particles.

7. The method of claim 1 wherein the contacting of particles of polysaccharide with the titanium compound in step (a) occurs after the reacting of the particles of polysaccharide with the derivatizing agent in step (b).

8. The method of claim 1 wherein the aqueous medium having an acidic pH comprises a Bronsted acid.

9. The method of claim 8 wherein the Bronsted acid is citric acid.

10. The method of claim 1 wherein the derivatized polysaccharide particle is a derivatized guar particle.

11. The method of claim 10 wherein the derivatized guar particle is selected from the group consisting of hydroxypropyl guar, carboxymethyl guar, hydroxyethyl guar, carboxymethylhydroxypropyl guar, hydroxybutyl guar, cationic guar, hydrophobically modified guar, hydrophobically modified carboxymethyl guar, hydrophobically modified hydroxyethyl guar, hydrophobically modified hydroxypropyl guar, hydrophobically modified carboxymethylhydroxypropyl guar, hydrophobically modified hydroxybutyl guar, and hydrophobically modified cationic guar.

12. The method of claim 1 further comprising:
    (f) washing the glyoxal crosslinked and derivatized particles concurrently with or after step (e).

13. The method of claim 1 wherein the step of contacting particles of a polysaccharide with a titanium compound is conducted in an aqueous medium having a pH greater than 10 under conditions appropriate to intra-particulately crosslink the particles.

14. The method of claim 13 wherein the step (e) comprises contacting the de-crosslinked particles with a glyoxal compound in an aqueous medium having a pH less than 7 under conditions appropriate to intra-particulately crosslink the particles.

15. The method of claim 13 wherein contacting the titanium crosslinked and derivatized particles with an aqueous medium in step (d), contacting the de-crosslinked particles with a glyoxal compound in step (e) or both is performed through spraying.

* * * * *